(12) United States Patent
Scott et al.

(10) Patent No.: US 11,768,110 B2
(45) Date of Patent: Sep. 26, 2023

(54) AIR QUALITY MONITORING SYSTEM AND METHOD

(71) Applicant: Project Canary, PBC, Denver, CO (US)

(72) Inventors: Anna Ailene Scott, Austin, TX (US); Yan Azdoud, Austin, TX (US); Christopher Daniel Kelley, Austin, TX (US)

(73) Assignee: Project Canary, PBC, Denver, CO (US)

( * ) Notice: Subject to any disclaimer, the term of this patent is extended or adjusted under 35 U.S.C. 154(b) by 0 days.

(21) Appl. No.: 18/113,311

(22) Filed: Feb. 23, 2023

(65) Prior Publication Data

US 2023/0213385 A1     Jul. 6, 2023

Related U.S. Application Data

(60) Continuation of application No. 17/962,171, filed on Oct. 7, 2022, now Pat. No. 11,604,094, which is a
(Continued)

(51) Int. Cl.
*G01J 3/26*        (2006.01)
*G01N 33/00*      (2006.01)
(Continued)

(52) U.S. Cl.
CPC ............ *G01J 3/26* (2013.01); *G01N 15/1404* (2013.01); *G01N 15/1436* (2013.01);
(Continued)

(58) Field of Classification Search
CPC ... G01J 3/26; G01N 15/1404; G01N 15/1436; G01N 33/0006; G01N 33/0031; G02B 26/001
(Continued)

(56) References Cited

U.S. PATENT DOCUMENTS 3,206,982 A    9/1965   Blondfield
3,662,171 A    5/1972   Brengman et al.
(Continued)

FOREIGN PATENT DOCUMENTS

CH            703014 A2    10/2011
CN          107782374 A    3/2018
(Continued)

OTHER PUBLICATIONS

U.S. Appl. No. 17/813,585, filed Jul. 19, 2022, Nathan C. Eichenlaub.
(Continued)

*Primary Examiner* — Md M Rahman
(74) *Attorney, Agent, or Firm* — Stephen B. Katsaros; Patent Engineering, LLC

(57) ABSTRACT

In an illustrative configuration, a method for monitoring air quality is disclosed. The method includes accepting analyte gas into a cell and reflecting light rays into the analyte gas repeatedly across the cell into at least one sensor. The light scattered by particulate matter in the analyte gas and amount of spectra-absorption due to presence of a gaseous chemical is then measured. Based on the determined amount of spectra-absorption and the measured scattered light the gaseous chemical is then measured.

21 Claims, 6 Drawing Sheets

Related U.S. Application Data division of application No. 17/716,326, filed on Apr. 8, 2022, now Pat. No. 11,467,032, which is a division of application No. 17/540,497, filed on Dec. 2, 2021, now Pat. No. 11,346,717, which is a continuation of application No. 16/953,908, filed on Nov. 20, 2020, now Pat. No. 11,193,822, which is a division of application No. 16/823,205, filed on Mar. 18, 2020, now Pat. No. 10,876,890, which is a division of application No. 16/188,793, filed on Nov. 13, 2018, now Pat. No. 10,634,558.

(51) Int. Cl.
G02B 26/00 (2006.01)
G01N 15/14 (2006.01)

(52) U.S. Cl.
CPC ..... *G01N 33/0006* (2013.01); *G01N 33/0031* (2013.01); *G02B 26/001* (2013.01)

(58) Field of Classification Search
USPC ............................................................. 356/454
See application file for complete search history.

(56) References Cited

U.S. PATENT DOCUMENTS

| | | | |
|---|---|---|---|
| 3,780,566 | A | 12/1973 | Smith et al. |
| 3,817,108 | A | 6/1974 | Principe et al. |
| 4,135,092 | A | 1/1979 | Milly |
| 4,551,719 | A | 11/1985 | Carlin et al. |
| 5,132,968 | A | 7/1992 | Cephus |
| 5,281,816 | A | 1/1994 | Jacobson et al. |
| 5,406,265 | A | 4/1995 | Trozzo et al. |
| 5,479,359 | A | 12/1995 | Rogero et al. |
| 5,568,121 | A | 10/1996 | Lamensdorf |
| 5,604,298 | A | 2/1997 | Dosoretz et al. |
| 6,061,141 | A | 5/2000 | Goldenberg et al. |
| 6,114,964 | A | 9/2000 | Fasano |
| 6,167,766 | B1 | 1/2001 | Dunn et al. |
| 6,169,488 | B1 | 1/2001 | Ketler |
| 6,252,510 | B1 | 6/2001 | Dungan |
| 6,259,956 | B1 | 7/2001 | Myers et al. |
| 6,317,029 | B1 | 11/2001 | Fleeter |
| 6,415,646 | B1 | 7/2002 | Kessel et al. |
| 6,490,530 | B1 | 12/2002 | Wyatt |
| 6,794,991 | B2 | 9/2004 | Dungan |
| 6,865,926 | B2 | 3/2005 | O'Brien et al. |
| 7,075,653 | B1 | 7/2006 | Rutherford |
| 7,080,544 | B2 | 7/2006 | Stepanik et al. |
| 8,485,019 | B2 | 7/2013 | Groves |
| 8,510,059 | B2 | 8/2013 | Prince |
| 8,712,335 | B2 | 4/2014 | Mathur et al. |
| 8,714,035 | B2 | 5/2014 | Mihaylav et al. |
| 8,949,037 | B2 | 2/2015 | Prince et al. |
| 9,018,963 | B2 | 4/2015 | Sim et al. |
| 9,075,016 | B2 | 7/2015 | Groves |
| 9,188,503 | B2 | 11/2015 | Kloepper et al. |
| 9,210,541 | B2 | 12/2015 | Root et al. |
| 9,754,472 | B2 | 9/2017 | Johnson et al. |
| 9,878,656 | B2 | 1/2018 | Gergets et al. |
| 9,978,251 | B2 | 5/2018 | Gonia et al. |
| 10,021,466 | B2 | 7/2018 | Guglielmo et al. |
| 10,031,040 | B1 | 7/2018 | Smith et al. |
| 10,089,849 | B2 | 10/2018 | Liu et al. |
| 10,119,890 | B2 | 11/2018 | Massengale et al. |
| 10,190,976 | B2 | 1/2019 | Waxman et al. |
| 10,210,738 | B2 | 2/2019 | Johnson, Jr. et al. |
| D842,134 | S | 3/2019 | Doi et al. |
| 10,371,682 | B2 | 8/2019 | Berndt et al. |
| 10,634,558 | B1 | 4/2020 | Scott et al. |
| 10,671,772 | B2 | 6/2020 | Luquist et al. |
| 10,697,947 | B1 | 6/2020 | Armitage |
| 10,814,028 | B2 | 10/2020 | Becker et al. |
| 10,876,890 | B2 | 12/2020 | Scott et al. |
| 11,193,822 | B2 | 12/2021 | Scott et al. |
| 11,215,593 | B2 | 1/2022 | Armitage |
| 11,366,057 | B2 | 6/2022 | Scott et al. |
| 11,408,870 | B2 | 8/2022 | Armitage |
| 11,573,157 | B2 | 2/2023 | Cyrus |
| 2001/0040509 | A1 | 11/2001 | Dungan |
| 2002/0070321 | A1 | 6/2002 | Womack |
| 2004/0056771 | A1 | 3/2004 | Dungan |
| 2006/0155486 | A1 | 7/2006 | Walsh et al. |
| 2008/0048853 | A1 | 2/2008 | Leach et al. |
| 2008/0231857 | A1 | 9/2008 | Depeursinge et al. |
| 2008/0278708 | A1* | 11/2008 | Vaidya ............... G01N 21/3577 356/51 |
| 2008/0281528 | A1 | 11/2008 | Relle, Jr. |
| 2009/0319058 | A1 | 12/2009 | Rovaglio et al. |
| 2010/0094565 | A1 | 4/2010 | Prince et al. |
| 2010/0268480 | A1 | 10/2010 | Prince |
| 2010/0295673 | A1 | 11/2010 | Ahmad |
| 2011/0219891 | A1 | 9/2011 | Mihaylov et al. |
| 2012/0012066 | A1 | 1/2012 | Beery et al. |
| 2012/0109583 | A1 | 5/2012 | Bartlett et al. |
| 2012/0212347 | A1 | 8/2012 | Boone |
| 2012/0227983 | A1 | 9/2012 | Lymberopoulos et al. |
| 2012/0270205 | A1 | 10/2012 | Patel et al. |
| 2014/0196788 | A1 | 7/2014 | Taft |
| 2014/0368354 | A1 | 12/2014 | Skourlis |
| 2015/0048232 | A1 | 2/2015 | Hallauer et al. |
| 2015/0185194 | A1 | 7/2015 | Prince et al. |
| 2017/0130480 | A1 | 5/2017 | Perkins |
| 2017/0277829 | A1 | 9/2017 | Weggler et al. |
| 2017/0336281 | A1 | 11/2017 | Waxman et al. |
| 2018/0266933 | A1 | 9/2018 | Tamraz et al. |
| 2018/0284735 | A1 | 10/2018 | Cella et al. |
| 2019/0110444 | A1 | 4/2019 | Boehm |
| 2019/0166413 | A1 | 5/2019 | Klinger et al. |
| 2019/0206068 | A1 | 7/2019 | Stark et al. |
| 2019/0360311 | A1 | 11/2019 | Cardenas et al. |
| 2019/0360924 | A1* | 11/2019 | Macrelli ................ H10N 10/80 |
| 2020/0333307 | A1 | 10/2020 | Armitage |
| 2020/0355580 | A1 | 11/2020 | Asher |
| 2021/0072080 | A1 | 3/2021 | Scott et al. |
| 2022/0034762 | A1 | 2/2022 | Cyrus et al. |
| 2022/0091026 | A1 | 3/2022 | Scott et al. |

FOREIGN PATENT DOCUMENTS

| | | | |
|---|---|---|---|
| CN | 207351764 | U | 5/2018 |
| CN | 109521162 | A | 3/2019 |
| CN | 209979311 | U | 1/2020 |
| CN | 212159251 | U | 12/2020 |
| CN | 214667980 | U | 11/2021 |
| CN | 214749208 | U | 11/2021 |
| DE | 10226305 | C1 | 10/2003 |
| DE | 102006034731 | A1 | 1/2008 |
| EP | 1882917 | A1 | 1/2008 |
| EP | 2687844 | A2 | 1/2014 |
| EP | 3001115 | A2 | 3/2016 |
| WO | 2022056152 | A1 | 3/2022 |

OTHER PUBLICATIONS

U.S. Appl. No. 17/813,602, filed Jul. 19, 2022, Nathan C. Eichenlaub.
U.S. Appl. No. 63/076,829, filed Sep. 10, 2020, Anna Ailene Scott.
U.S. Appl. No. 63/233,694, filed Aug. 16, 2021, Anna Ailene Scott.
"Operational risk management in the energy industry," 2014, Management Solutions, 10 pages (Year: 2014).
Center for Chemical Process Safety, "Guidelines for Chemical Process Quantitative Risk Analysis, Second Edition," "Chapter 1, Chemical Process Quantitative Risk Analysis," 2010, American Institute of Chemical Engineers, pp. 1-55 (Year: 2010).
Center for Chemical Process Safety, "Guidelines for Chemical Process Quantitative Risk Analysis, Second Edition," "Chapter 3, Event Probability and Failure Frequency Analysis," 2010, American Institute of Chemical Engineers, pp. 297-393 (Year: 2010).
Collier-Oxandale, et al., "Understanding the ability of low-cost MOx sensors to quantify ambient VOCs", Atmospheric Measurement Techniques, Mar. 5, 2019, pp. 1441-1460, vol. 12, Copernicus

(56) References Cited

OTHER PUBLICATIONS

Publications on behalf of the European Geosciences Union, 20 pages.
Control Effectiveness, May 2014, Broadleaf Capital International Pty Ltd, 7 pages (Year: 2014).
Ebermann et al., "Design, Operation and Performance of a Fabry-Perot-Based MWIR Microspectrometer," access date: Nov. 9, 2018, pp. 1-6.
F. I. Khan et al., "Safety weighted hazard index (swehi) a new, user-friendly tool for swift yet comprehensive hazard identification and safety evaluation in chemical process industries," 2001, Transactions of the Institution of Chemical Engineers, vol. 79 Part B, 16 pages (Year: 2001).
Faisal I. Khan et al., "Multivariate hazard identification and ranking system," 1998, Process Safety Progress, vol. 17, No. 3, 14 pages (Year: 1998).
FAQ, Meet Clair Site, access date: Nov. 9, 2018, pp. 1-8.
International Search Report and Written Opinion from the US International Search Authority for International Application No. PCT/US2020/012247 dated Mar. 10, 2020, 13 pages.
ISA/US, International Search Report and Written Opinion for PCT/US21/49702, dated Feb. 7, 2022, 36 pages.
Jim Joy et al., "National minerals industry safety and health risk assessment guideline" 2007, http://www.nost.edu.au/icms_docs/286339_National_M inerals_Industry _ Safety _and_Health_Risk_ Assessment_ Guideline_ -_J im_Joy.pdf, 164 pages (Year: 2007).
JJS Technical Services, "BW Technologies Rig Rat III Gas Detector (Non-Wireless Version)", , retrieved from the Internet Jul. 19, 2019, 3 pages.
Maureen Hassall, "What is a control?," Aug. 31, 2015, 2015 NSW Mining-Health, Safety, Environment and Community Conference, 33 pages (Year: 2015).
Mohammad Javad Jafari et al., "The credit of fire and explosion index for risk assessment of iso-max unit in an oil refinery, 2012, International Journal of Occupational Hygiene," vol. 4, No. 1, pp. 10-16 (Year: 2012).
Restek Pure Chromatography "TO—Can Canister With Rave Valve cat.# 27416, 27417, 27418, 27419, 27420, 27421, 27422, 27423" Catalog #500-10-002 Date Oct. 2020.
S.M. Miri Lavasani et al., "Fuzzy risk assessment of oil and gas offshore wells," 2011, Process Safety and Environmental Protection , vol. 89, pp. 277-294 (Year: 2011).
Sam Mannan, "Lee's loss prevention in the process industries," 2012, Butterworth-Heinemann, 8 pages (Year: 2012).
Scott et al., "An Air Quality Sensor Network for Greater Baltimore," access date: Nov. 9, 2018, pp. 1-8.
Scott, Meet Clair Site, What causes trouble breathing indoors? blog, access date: Nov. 9, 2018, pp. 1-8.
U.S. Environmental Protection Agency, "Determination of Volatile Organic Compounds (VOCs) in Air Collected in Specially Prepared Canisters and Analyzed by Gas Chromatography—Mass Spectrometry (GC-MS)" Sep. 2019.
United States Environmental Protection Agency, "SPod Fenceline Sensors Under Development", , retrieved from the Internet Jul. 19, 2019, 1 page.
United States Environmental Protection Agency, "Tracking Emissions Using New Fenceline Monitoring Technology", published Jun. 18, 2018, , retrieved from the Internet Jul. 19, 2019, 3 pages.
Wisconsin Department of Natural Resources, "Evaluation of Passive Sampling Techniques for Monitoring Roadway and Neighborhood Exposures to Benzene and Other Mobile Source VOCs" WDNR Publication AM-384 2007.
Zimmerman et al., Atmospheric Measurement Techniques, "A machine learning calibration model using random forests to improve sensor performance for lower-cost air quality monitoring," Jul. 25, 2017, pp. 291-313.

* cited by examiner

AIR QUALITY MONITORING SYSTEM AND METHOD

CROSS-REFERENCE TO RELATED APPLICATIONS

This application is a continuation of patent application Ser. No. 17/962,171, filed on Oct. 7, 2022, and entitled "Air Quality Monitoring System And Method", which is a divisional of and claims priority under 35 U.S.C. § 120 to pending U.S. patent application Ser. No. 17/716,326, filed on Apr. 8, 2022, and entitled "Air Quality Monitoring System and Method," (now U.S. Pat. No. 11,467,032, issued on Oct. 11, 2022), which is a divisional of patent application Ser. No. 17/540,497, filed on Dec. 2, 2021, and entitled "Air Quality Monitoring System and Method," (now U.S. Pat. No. 11,346,717, issued on May 31, 2022), which is a continuation of patent application Ser. No. 16/953,908, filed on Nov. 20, 2020, and entitled "Air Quality Monitoring System Enhanced Spectrophotometric Chemical Sensor" (now U.S. Pat. No. 11,193,822, issued on Dec. 7, 2021), which is a division of U.S. patent application Ser. No. 16/823,205, filed on Mar. 18, 2020, and entitled "Air Quality Monitoring System and Enhanced Spectrophotometric Chemical Sensor," (now U.S. Pat. No. 10,876,890, issued on Dec. 29, 2020), which is further a divisional of and claims priority under 35 U.S.C. § 120 to U.S. patent application Ser. No. 16/188,793, filed on Nov. 13, 2018, and entitled "Air Quality Monitoring System and Enhanced Spectrophotometric Chemical Sensor" (now U.S. Pat. No. 10,634,558, issued on Apr. 28, 2020).

A portion of the disclosure of this patent document contains material, which is subject to copyright and/or mask work protection. The copyright and/or mask work owner has no objection to the facsimile reproduction by anyone of the patent document or the patent disclosure, as it appears in the Patent and Trademark Office patent file or records, but otherwise reserves all copyright and/or mask work rights whatsoever.

BACKGROUND

Air quality is one of the most important factors that can affect the health of a population. Countries around the world spend significant resources on monitoring air quality and controlling air pollution. One of the major problems is that instruments that can accurately monitor air quality are expensive and typically require expertise to operate properly. Currently, air quality monitoring is mainly performed by government agencies and dedicated organizations using specialized instrumentation. As a result, general air quality data often does not provide the fidelity necessary to pinpoint issues in a scale smaller than a regional level. Because air quality monitoring instruments are so expensive, most people typically do not have the means to obtain the data needed to identify air quality issues on an individual basis.

SUMMARY

Described herein is an air quality monitoring system that enables a wide scale deployment of monitors with enough accuracy for meaningful and actionable data. In one aspect, an advanced technique is used to calibrate low-precision gaseous chemical sensors to obtain accurate measurements by cross-calibrating those sensors to correct sensitivities to parameters that cause errors to measurements of targeted chemicals. In another aspect, air quality measurements are used to identify sources of chemicals in a localized level by accounting for local conditions using data such as ambient condition data and user-provided data about the local environment. In yet another aspect, a gaseous chemical sensor with an improved encasement having a cell for reflecting and lengthening light path is provided to reduce the limitations and enhance the accuracy of a conventional spectrophotometric gaseous chemical sensor.

The system and components described herein reduce the resources (e.g., instrument setup time, cost, expertise) that are needed to deploy a large-scale air quality monitoring system and to increase fidelity of air quality data. Reducing the need for resources also enables new ways of gathering air quality data, such as by crowd-sourcing data from instruments deployed by average users. The invention also serves to democratize air quality monitoring by making air quality instrumentation and analysis affordable to individual users.

BRIEF DESCRIPTION OF THE DRAWINGS

The accompanying figures of the drawing, which are included to provide a further understanding of general aspects of the system/method, are incorporated in and constitute a part of this specification. These illustrative aspects of the system/method, and together with the detailed description, explain the principles of the system. No attempt is made to show structural details in more detail than is necessary for a fundamental understanding of the system and various ways in which it is practiced. The following figures of the drawing include.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label. Where the reference label is used in the specification, the description is applicable to any one of the similar components having the same reference label.

DETAILED DESCRIPTION

Illustrative configurations are described with reference to the accompanying drawings. Wherever convenient, the same reference numbers are used throughout the drawings to refer to the same or like parts. While examples and features of disclosed principles are described herein, modifications, adaptations, and other implementations are possible without departing from the spirit and scope of the disclosed configurations. It is intended that the following detailed description be considered as exemplary only, with the true scope and spirit being indicated by the following claims.

Figure 1:
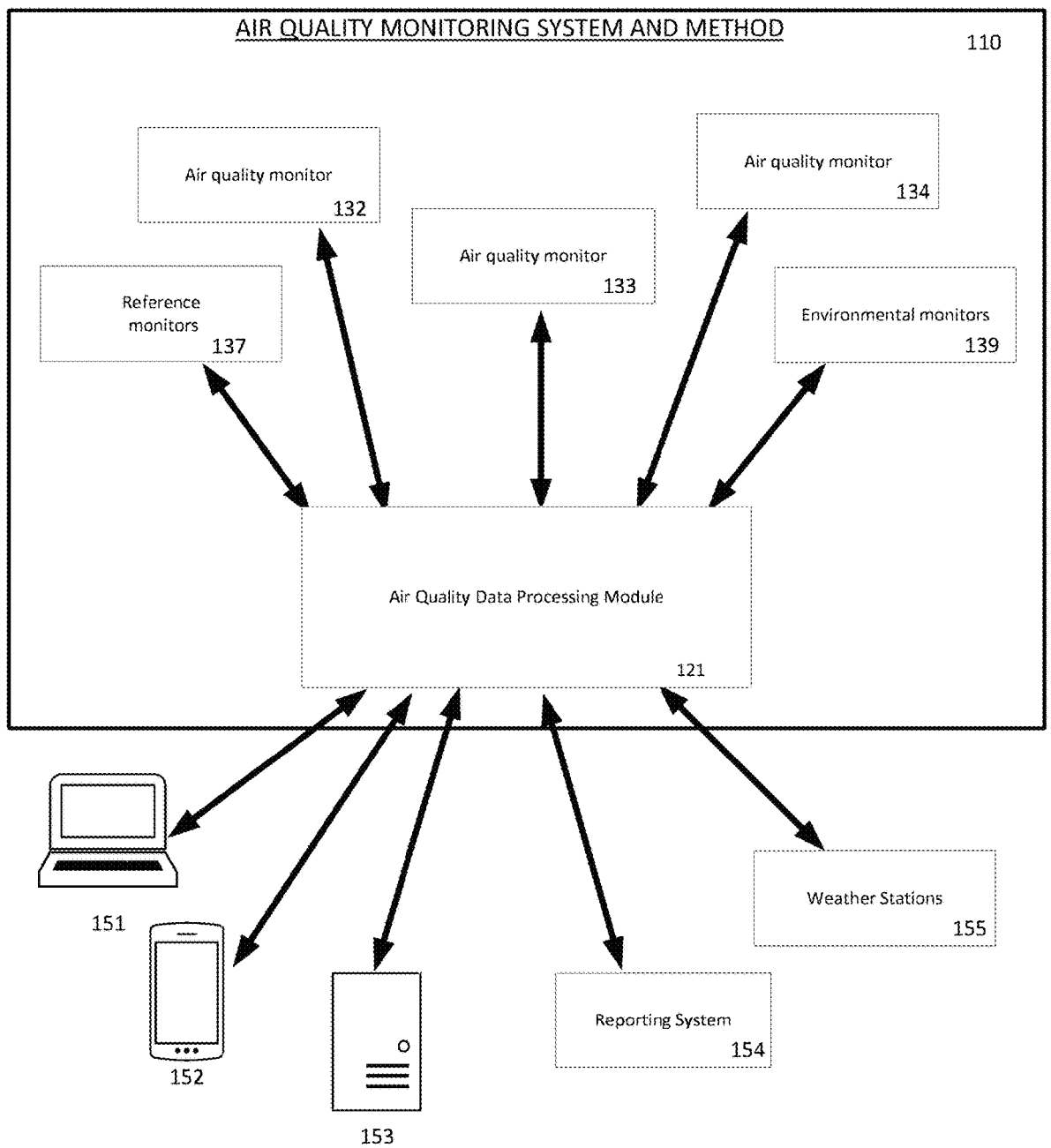
FIG. 1 shows an example of an air quality monitoring system.

FIG. 1 shows an example of an air quality monitoring system 110, which handles air quality data from different sources. As illustrated in FIG. 1, air quality monitoring system 110 may include an air quality data processing module 121, a plurality of air quality monitors 132-134, reference monitors 137 and environmental monitors 139. Air quality monitors 132-134 can include one or more chemical sensors configured to detect and measure chemicals, such as ozone, nitrogen oxide, carbon dioxide, sulfur dioxide, volatile organic compounds, methane or other hydrocarbons, and other chemicals in gaseous state (these are herein being described as gaseous chemicals), as well as one or more particle sensors configured to detect and measure the presence of suspended particles in air such as dust, smoke, pollen, or soot (these are herein described as particulate matter or PM). Air quality monitors 132-134 may include an enhanced gaseous chemical sensor having a multi-pass cell for light rays, as will be described in more detailed below, such as in conjunction with FIG. 6. Air quality monitors 132-134 may be located at multiple different locations. For example, multiple monitors may be located around a sizable area, such as a county, a city or a neighborhood. Several instruments may also be located within a building or a dwelling.

Reference monitors 137 include precision gaseous chemical sensors and are configured to provide measurements for use in calibrating the gaseous chemical sensors in air quality monitors 132-134. Environmental monitors 139 are configured to measure environmental conditions, such as humidity, temperature, atmospheric pressure, air density, light, location, wind speed, and the like.

Air quality data processing module 121 is configured to communicate with air quality monitors 132-134, reference monitors 137, and environmental monitors 139. For example, air quality data processing module 121 may receive data from these monitors, such as measurements. Air quality data processing module 121 may also transmit data to these monitors, such as providing calibration data. Air quality data processing module 121 can correct measurements from air quality monitors 132-134 using cross-calibration factors, as will be explained below. Air quality data processing module 121 is also configured to process the data from monitors and perform analysis to calculate or infer additional air quality data such as the amount of various gaseous chemicals in various locations, sources of those gaseous chemical, and recommendations based on elicited requirements or preferences of end users. Air quality data processing module 121 is configured to communicate with mobile devices 152, computing devices 151 and server devices 153 to receive data and provide received, calculated, and inferred air quality data. For example, air quality data processing module 121 may receive user-input data and use that data to derive additional air quality data relevant to the area of analysis. Air quality data processing module 121 is also configured to communicate with other sources of data such as reporting system 154 and weather stations 155. Air quality data processing module 121 may be implemented in any appropriate physical or virtual computing platform (such as a networked server), and may operate and act through any suitable interface (such as a cloud computing platform).

Air quality monitoring system 100 may also be configured to process incoming data to provide a variety of outputs. For example, air quality monitoring system may analyze measurements from air quality monitors 132-134 to determine sources of the gaseous chemicals being detected. Air quality monitoring system may provide actionable steps to affect the chemical sources, such as ways to reduce the release of those chemicals or ways to minimize exposure to those chemicals, making use of stated preferences or user requirements, and/or ancillary (e.g. topological, geological, meteorological, demographic) datasets relevant to the area of investigation.

Figure 2:
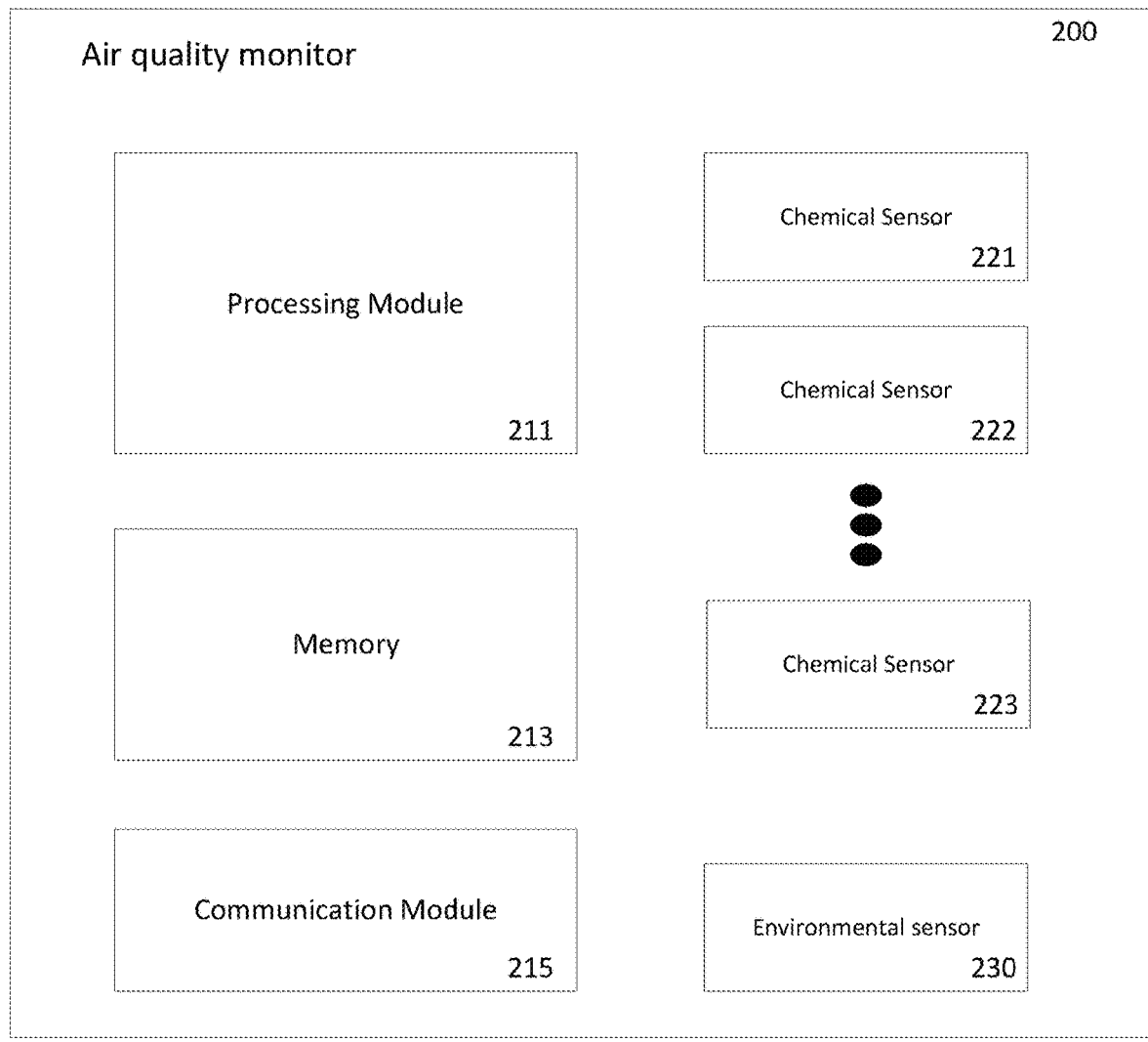
FIG. 2 shows an example air quality monitor and some example components that may be included.

FIG. 2 shows an example air quality monitor 200 (such as air quality monitors 132-134 in FIG. 1) and some example components that may be included. Air quality monitor 200 may include processor module 211, memory 213, communication module 215, and one or more gaseous chemical sensors, such as gaseous chemical sensors 221-223, and environmental sensor 230. Processor module 211 processes computing tasks and controls other components. The computing tasks may include data calibration. Memory 213 stores data, such as measurement data from gaseous chemical sensors 221-223 and calibration data such as cross-calibration factors. Gaseous chemical sensors 221-223 are configured to measure gaseous chemicals in analyte gas, such as gas under sampling by air quality monitor 200. Environmental sensor 230 measures environment conditions, such as temperature, pressure, humidity, location, wind speed, and the like. Communication module 215 handles communication with other devices. For example, communication module 215 may handle communication between air quality monitor 200 and air quality data processing module 121, other air quality monitors, user-devices such as mobile devices 151 and computing devices 152, and the like. Communication module 215 may communicate through any of a variety of wired and wireless mechanisms, such as Wi-Fi, Bluetooth, mobile networks, and the like. Air quality monitor 200 may also be configured to measure time, position and other relevant information for computing devices.

Figure 3:
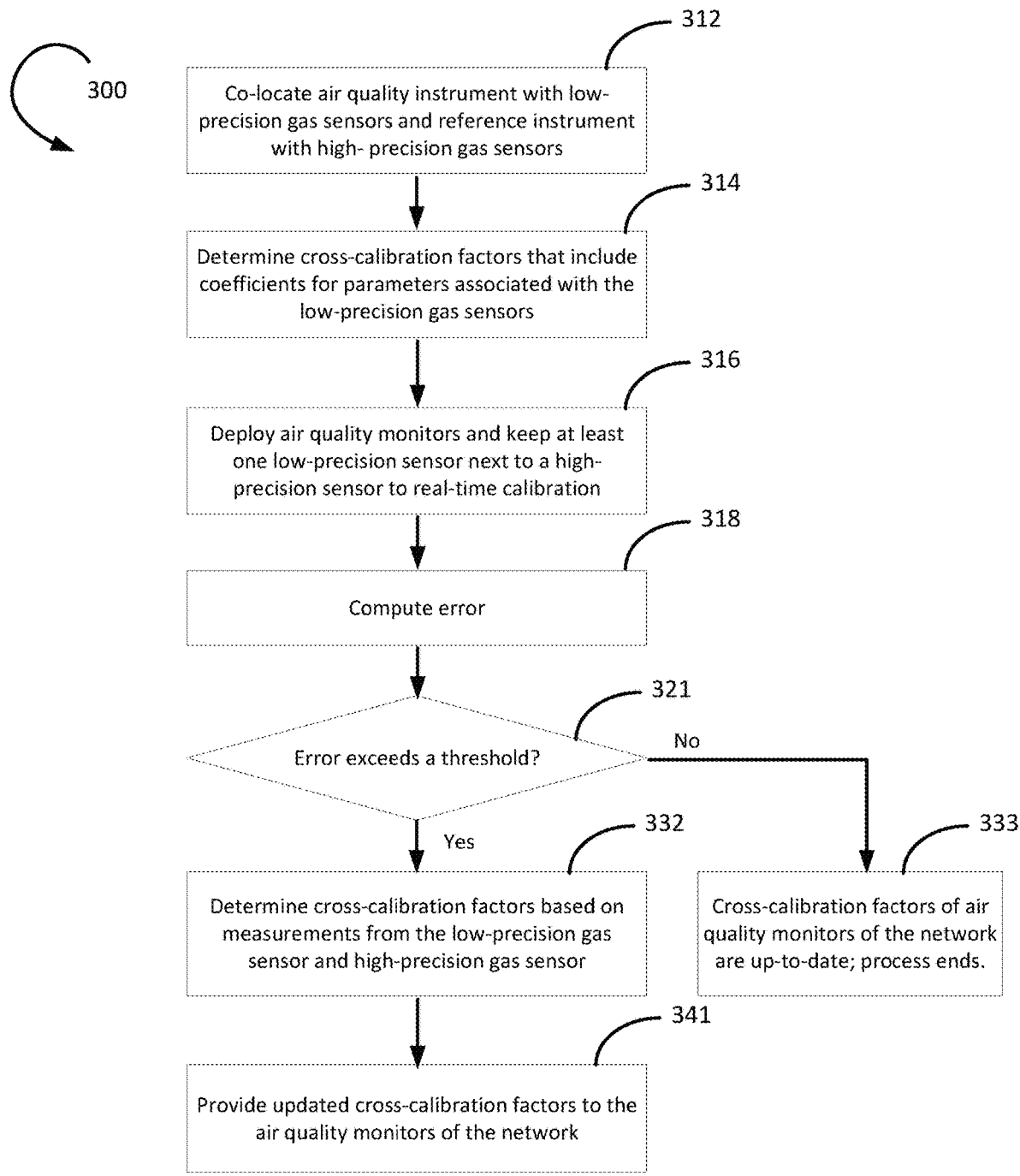
FIG. 3 shows a flow chart of an example cross-calibration method for calibrating a gaseous chemical sensor in an air quality monitor.

Gas Sensor Calibration Process:

Air quality monitoring system 110 is configured to increase the accuracy of low-precision gaseous chemical sensors through cross-calibration. Operators of air quality monitoring system 110 may implement a cross-calibration method 300 as shown in FIG. 3. This cross-calibration method 300 can improve the accuracy of low-precision gaseous chemical sensors, which are sensitive to both their target gas as well as additional parameters, including (but not limited to) other gases, changes in environmental conditions (wind, pressure, humidity/moisture), or radio waves. Cross-calibration method 300 calculates sensitivity of one of the gaseous sensors to the target gas as well as confounding factors, and deduce the true value of the target gas by, for example, placing air quality monitors with low-precision gaseous chemical sensors next to a reference monitor with high-precision sensors.

Example equations for calculating cross-calibration factors and errors for calibration are shown below. According to the cross-calibration method, a low-precision sensor tasked with measuring a gas concentration X is sensitive to additional parameters y1, y2, yn, as illustrated in equation 1. In practice, one or more air quality monitors and one or more reference monitors may be used. The air quality monitors with low-precision gas sensors are placed next to reference monitors with high precision gas sensors which are not sensitive to these additional parameters. The calibration method determines the concentration of gas X as a function of the measured concentration y0 and additional parameters y1, y2, yn using equation 1. Coefficients a0, a1 . . . , an are determined where these coefficients represent sensitivity of the low precision sensor to parameter y1, y2, . . . , yn.

$$Y_0 = a_0 X + a_1 y_1 + a_2 y_2 + \ldots + a_n y_n \qquad \text{Equation 1}$$

After the air quality monitors are deployed in the network, an air quality monitor with low-precision gaseous chemical sensors may be placed next to a reference monitor with high-precision gaseous chemical sensors. The error between the high-precision monitor and the low-precision monitor may be calculated using equation 2 below:

$$E = X' - 1/a_0(y_0 - a_1 y_1 - \ldots - a_n y_n) \qquad \text{Equation 2}$$

If the error is nonzero, the cross-calibration method is performed for this pair of low-precision sensor and reference sensor. The difference in original and updated parameters y1, yn is reported and then pushed to devices on the network. For a naive implementation, only the error ε is applied as a correction to the network of air quality monitors with similar low-precision gaseous chemical sensors, though more involved methods may be used.

Figure 4A:
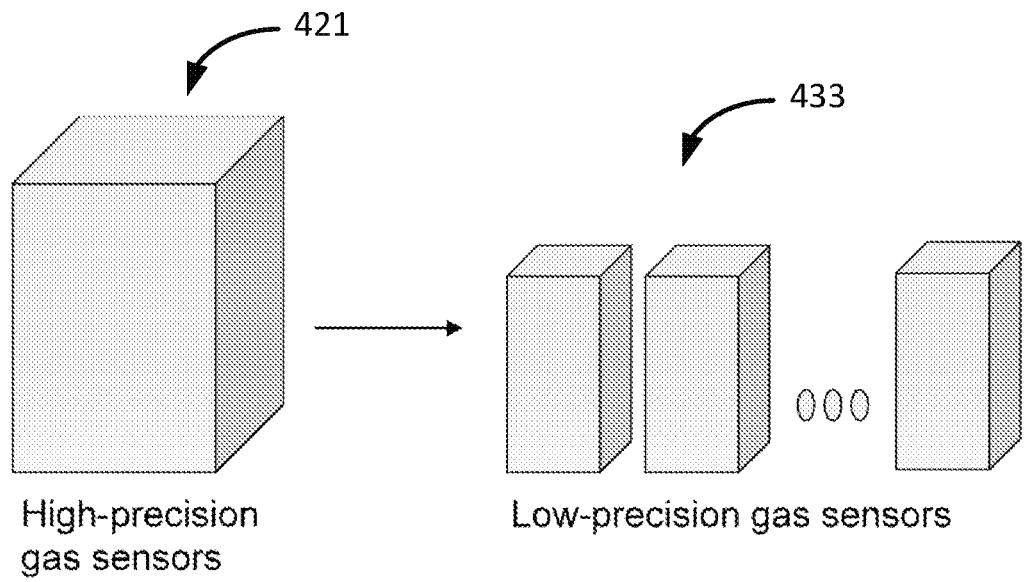
FIG. 4A shows an overview of sensor calibration.

In the air quality monitor network, the cross-calibration method 300 can be implemented by first placing each of the air quality monitors next to a reference monitor to calculate coefficients of the parameters for calibration. As shown in step 312 and illustrated in FIG. 4A, cross-calibration begins by co-locating low-precision gaseous chemical sensors and high-precious gaseous chemical sensors. These sensors can be co-located using any of a variety of different configurations, such as by themselves, while incorporated in air quality monitors and reference monitors, a mix of different configurations, and the like.

At step 314, cross-calibration factors are determined. Cross-calibration factors may include coefficients for parameters associated with the low-precision gaseous chemical sensors. These cross-calibration factors may be implemented in any of a variety of ways and data structures, such as being simple values of the coefficients, combining the coefficients with the parameters, as an array of values, and the like. These cross-calibration factors may be used by individual air quality monitors, air quality data processing modules, other systems to calibrate and correct measurements of low-precision sensors of air quality monitors, and the like.

Figure 4B:
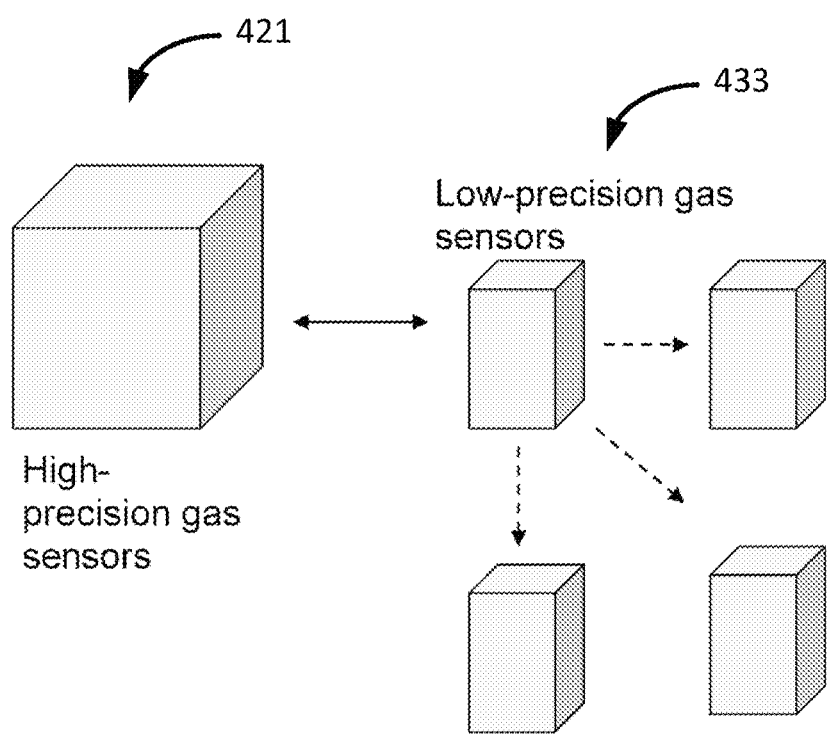
FIG. 4B shows an overview of sensor calibration update.

At step 316, the air quality monitors are deployed in the network. As shown in FIG. 4B, one or more selected low-precision gas sensors 433 may be kept in proximity to one or more reference monitors 421 for updating cross-calibration after deployment.

Cross-calibration method 300 can calculate updated coefficients in real-time and apply that update to the network of air quality monitors. For example, at step 318, an error is computed to determine if the cross-calibration factors require an update. The error may be calculated using example equation 2 and as discussed above.

At decision step 321, a determination is made whether the error exceeds a threshold. An error that exceeds a threshold indicates that the cross-calibration factors may require an update. If the error exceeds the threshold and an update is needed, method 300 moves to step 332 where the cross-calibration factors are updated based on measurements from the low-precision gaseous chemical sensor and high-precision gaseous chemical sensor that were co-located after deployment for calibration updating purpose, as discussed in connection with step 316 and FIG. 4B. At step 341, the updated cross-calibration factors are provided to the air quality monitors of the network and the process ends.

Back at decision step 321, if the error is below the threshold, method 300 moves to step 333 where cross-calibration factors of air quality monitors of the network are up-to-date and the process ends.

Cross-calibration method 300 above may be implemented in any of a variety of different ways by different devices in any combinations. For example, air quality data processing module may implement this process to initially calibrate the air quality monitors by determining the cross-calibration factors and then updating the air quality monitors in a periodic basis. The air quality data processing module may correct data received from the deployed air quality monitors based on the updated cross-calibration factors, push these updated factors to the deployed air quality monitors so that the monitors can update the data before sending to the air quality data processing module and other devices, a combination of correction steps, and the like.

Gas Sensors Calibration Examples:

The below examples illustrate some possible implementation scenarios of the calibration process and example capabilities of the air quality monitoring system.

Calibration Example 1

A low-precision ozone sensor is sensitive to rapid changes in humidity and nitrogen dioxide. Using a high precision instrument, the process calculates sensitivity of the sensor to ozone, humidity changes, and nitrogen dioxide. The process uses these values to eliminate humidity changes and nitrogen dioxide from the values returned by the low-precision ozone sensor and deduce the true ozone value.

Calibration Example 2

A low-precision sulfur dioxide sensor is sensitive to changes in humidity and passing radio waves. The system combines the sulfur dioxide sensor with a humidity sensor, and a hydrogen sulfide sensor with similar material properties—hydrogen sulfide (outside of sewers and marshes) is low in the environment. The process calculates the sensitivity of the hydrogen sulfide sensor to sulfur dioxide and the sensitivity of the sulfur dioxide sensor to humidity changes. When the sulfur dioxide sensor reads high and hydrogen sulfide reads high, the system ignores the sulfur dioxide reading, assuming that a passing radio wave is setting off the system. When the sulfur dioxide sensor reads high and hydrogen sulfur sensor reads low, then a sulfur dioxide reading is confirmed.

Calibration Example 3

A network of air quality monitors is installed in a city. One of the air quality monitors is placed next to a reference monitor with high-precision gas sensors. Periodically (e.g., every minute), the error between the air quality monitor and the reference monitor is calculated and applied as a correction to other air quality monitors in the network.

Figure 5:
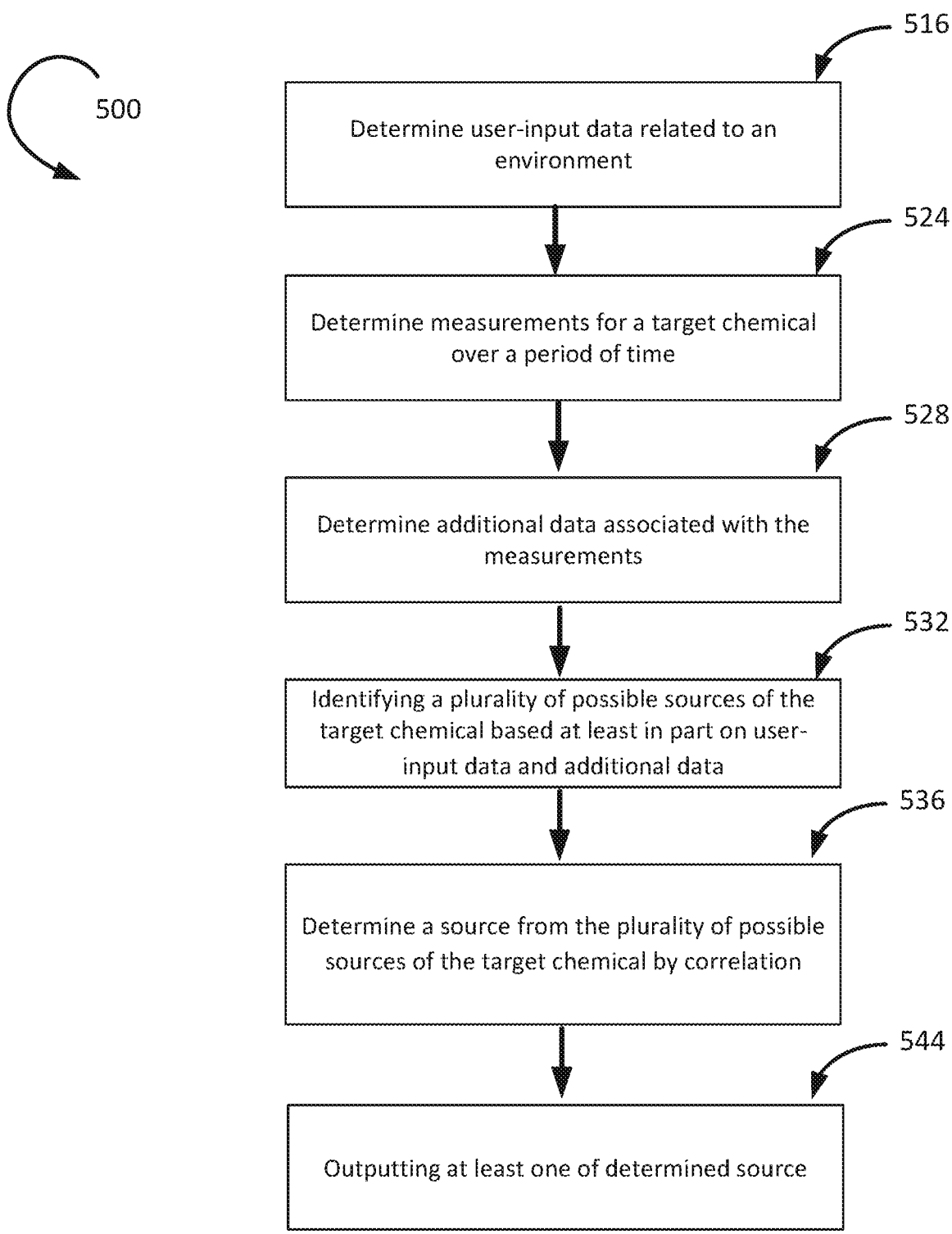
FIG. 5 shows a flow chart of an example source determination method.

Source Determination and Action Recommendation Process:

Air quality monitoring system 110 is configured to determine sources of gas that are detected by air quality monitors. An example source determination method 500 is shown in FIG. 5. At step 516, user-input data related to an environment is determined. The user-input data may include any type of input about the environment, as such conditions associated with one or more air quality monitors deployed around a location. User-input data can include any of a variety of types of data such as:

1. type and location of objects, such as newly installed carpet that can out-gas chemicals;
2. events that can cause chemicals in the air, such as cleaning using chemical products;
3. layout of the location, such as the placement of vents, windows, and doors; and
4. users' personal data, such as allergies, medical conditions, health concerns, daily routines, travel plans, and the like.

Air quality monitoring system 100 may receive this data in any of a variety of way, such as through a website, an application installed on a mobile device, automatically from home sensors or mobile devices, information from other systems and services, and the like.

At step 524, the source determination method 500 determines measurements for a target gaseous chemical over a period. These measurements may be provided by air quality monitors of air quality monitoring system 110. At step 528, additional data associated with the measurements are determined. The additional data may include data from a variety of sources that are relevant to determining sources of gaseous chemicals measured by air quality monitoring system 110. The additional data may come from any of a variety of sources, such as weather data from weather stations, traffic data from traffic management administration, chemical events such as from government reporting agencies, online services such as social network, and the like.

At step 532, a plurality of possible sources of the target chemical are identified based at least in part on the user-input data and additional data. At step 536, one or more sources from the plurality of possible sources of the target chemical are identified by correlation. The correlation may be determined between the measured data from an air quality monitor, user-input data and additional data. For example, the presence and amount of a gaseous chemical may correlate to an event or an object at the proximate location and at around the same time. The correlation process may be implemented in any of a variety of ways. An example process is shown below along with example equations that illustrate the methodology. Artificial intelligence algorithms and cloud-based data analytics may be employed as part of the correlation process.

At step 544, at least one determined source is output. The source may be output in any of many different ways, such as data to a service, a website, a user-interface on a mobile app and the like. Source determination method 500 may also provide recommendations, such as to reduce the gaseous chemical from the source, reduce exposure to the gaseous chemical, and the like. Examples are provided in the source determination examples below.

Correlation Process and Calculations:

An example of correlation steps and calculations are provided below:

1) Sort training data into categories using a clustering algorithm, such as a k-means clustering approach. Given a set of d parameters and n observations of each parameter, we solve the following minimization equation to cluster the data into k sets S. This is done by finding means mu:

$$\mathrm{argmin}_S \sum_{i=1}^{k} \sum_{X \in S_i} \|X - \mu\|^2 = \mathrm{argmin}_S \sum_{i=1}^{k} |S_i| \sigma^2 S_i$$

2) In real-time, feed in data. Using the categorization established in (1), determine which category Si variable x is most likely to fit into by solving for i:

$$\min \sum_{i=1}^{k} \sum_{X \in S_i} \|X - \mu\|^2$$

3) Map categorization S to solutions S' using scientific literature reviews, best practices from experts, and clinical guidelines.

Source Determination and Action Recommendation Examples:

The below examples illustrate some possible implementation scenarios of the chemical source differentiation process and example capabilities of the air quality monitoring system.

Source Determination and Action Recommendation Example 1:

A volatile organic compound (VOC) sensor detects a large, quick increase in VOC concentration that quickly dissipates. By taking into account the concentration, change of concentration over time, and time of the signal, the process determines that the source is most likely to be a consumer cleaning product.

Source Determination and Action Recommendation Example 2:

Detecting high VOC concentrations in an indoor environment, the air quality monitoring system recommends that individuals open a window to increase airflow and reduce their health exposure.

Source Determination and Action Recommendation Example 3:

The air quality monitoring system detects high temperature, pressure and ozone levels outdoors characteristic of stationary pressure weather system during the summertime on the East Coast. The system determines that the high ozone levels are most likely due to high levels of ozone being blown into the area, coupled with high levels of traffic. The system recommends that the city increase carpooling and public transportation use.

Source Determination and Action Recommendation Example 4:

The air quality monitoring system detects moisture, pressure, and high levels of particulate matter during an early fall cold spell in the Pacific Northwest. It deduces that an inversion layer is responsible for the buildup in pollution and suggests that the city reduce biomass burning to reduce pollution (e.g., what is colloquially referred to as a 'burn ban').

Source Determination and Action Recommendation Example 5:

The air quality monitoring system detects high levels of particles and nitrogen dioxide in India in the winter. The system recommends that users wear a protective mask to lower their health exposure to pollution.

Enhanced Gaseous Sensor with Paired Spectrophotometry and Nephelometry

The air quality monitoring system described herein may include an enhanced gaseous chemical sensor configured as a low-maintenance spectrophotometer and nephelometer that identifies gaseous chemicals by their light absorption spectrum and particulate matter by their scattering spectrum. The gaseous chemical sensor described below is a gaseous chemical sensing device for measuring chemicals in air. It includes a light source that emits light rays and a spectrophotometric detector. The chemical sensor also includes a cell having two reflective surfaces located at opposite ends of the cell. The reflective surfaces are configured to reflect the light rays along a path across the cell and to direct the light rays to the spectrophotometric detector. This cell enables light rays to pass through the analyte gas multiple times to enable more accurate measurements and to minimize the interference of particulate matter in the analyte gas with respect to the spectroanalysis. The configuration of the cell also enables the measurement of particulate matter in the analyte gas, for example, a sensor that measures light scattered by particulate matter that intercepts the light rays along the path.

Figure 6:
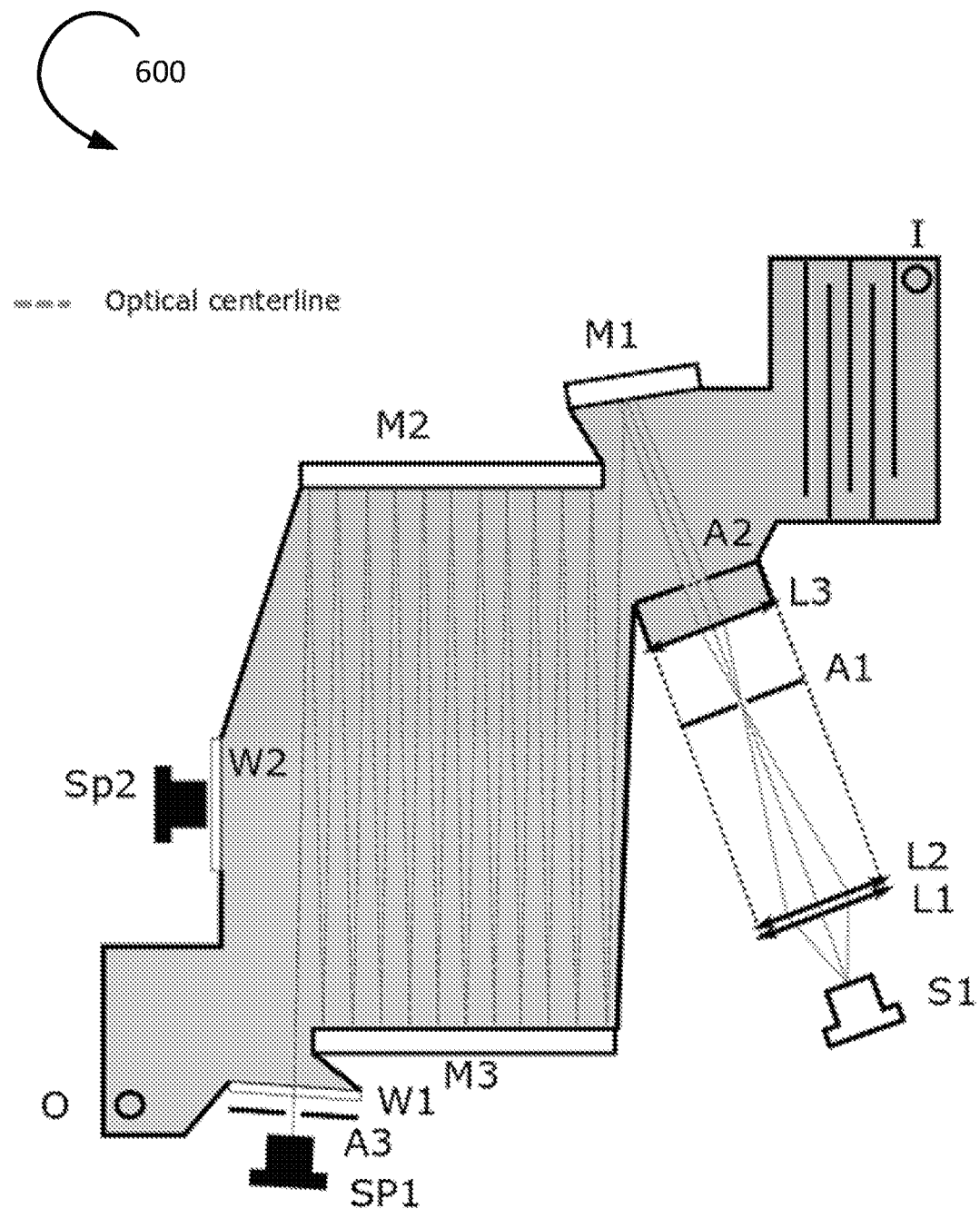
FIG. 6 shows an example of an example gaseous chemical sensor with example components.

The chemical sensor also includes an analyzer that measures at least one chemical by receiving measurements made by the spectrophotometric detector. It is configured to determine the amount of spectro-absorption due to presence of the at least one gaseous chemical and compensate for presence of the particulate matter based on amount of scattered light measured by the photo detector. An example gaseous chemical sensor that can be implemented in an air quality monitor and example components of the sensor are illustrated in FIG. 6 and described in more detailed below. The example components illustrated in FIG. 6 include:

I: Gas intake followed by an inertial trap for large particulate matter
0: Gas output (where the analyte is pumped out)
S1: Broadband light source
A1, A2, A3: Round apertures to improve coherence
L1, L2, L3: Convex lenses for the collimator/concentrator system; L3 serves as seal
M1: Alignment mirror to inject the collimated rays in the multi-pass mirror cell
M2, M3: pair of flat or concave mirrors forming a multi-pass mirror cell
for path length extension.
W1, W2: Observation windows for the spectrometers
SP1, SP2: Spectrophotometer sensors; SP2 acts alternately as a nephelometer Optical Description Light is produced by the light source S1 and collimated into (close to) parallel rays by the optical system formed by L1, L2, L3, A1 and A2. The light source may have a reflector to improve light concentration. The chosen layout of lenses and apertures concentrate the collimated light into a tighter beam as well. Any other system of optical elements may be used to generate the light collimation and concentration, or other broadband sources of collimated light such as a laser comb may be employed.

The rays of light, concentrated and collimated, are injected in a multi-pass mirror cell. Such a cell may use flat or focusing mirrors M2, M1 such as convex mirrors (as with a Herriott cell, White cell, Pfund cell or circular multi-pass cell). The cell is configured to increase the pathlength of light passing through the analyte gas. The longer pathlength increases absorption and Signal-to-Noise Ratio (SNR). The rays of light, after exiting the cell, are directed toward the spectrophotometer sensor SP1. This sensor and accompanying digital circuitry determine the intensity and spectral distribution of light that travelled from the source and through the analyte gas. Sensor SP2 analyzes the spectrum and intensity of light rays scattered by any particulate matter present in the analyte gas traveling through the system from I to 0. Micro-spectrophotometers, such as a Fabry-Perot Interferometer (FPI, such as those made by the manufacturer Infratec) or diffraction grating-based micro-spectrophotometers (such as those made by manufacturer Hamamatsu) among others, may be suitable for SP1 and SP2.

Structural Description

The body of the device separates the optics and electronics from the environment, exposes the optical cell to the pumped gas analyte, rigidly maintains alignment of the optical elements, and limits the influence of stray light rays on the light spectrum emitted by S1. The body of the device can be built as a single structural unit with top and bottom plates for sealing. The body may be built out of various rigid materials, and can be 3d-printed, machined, molded, injected, extruded, or produced through other suitable processes. Interface elements are used to connect the optical elements to the body. The structure may also be optimized to limit the upper bound of particulate matter in the device body without placing filters on the input analyte gas channel.

For sealing, gaskets may be used between the mirror cell (exposed to the analyte gas), the environment and the optics and electronics (maintained in a dry atmosphere). Certain optical elements, such as the observation windows W1 and W2 and the lens L3, provide as an interface between the optical chamber and the rest of the system, and may be used as seals.

For optics alignment, the structure is rigidly constructed and may use symmetries, topology optimization and low thermal expansion materials to limit misalignment of the optical elements during the lifetime of the device. Interface elements in the form of adjustable mounting plates act as optical holders for precise alignment and calibration. These plates may be machined to fit the optical elements precisely and may be linked to the main body with screws, bolts or other fastening systems. The plates are set in place in the body such that the described optical path is realized, and their positions can be calibrated at assembly and during periodic maintenance.

For stray light ray limitation, the entire body of the device in the optical cell may be coated with a light-absorbing coating with low reflectivity in the observational band of interest. This can be achieved by a variety of ways, such as by anodization, by deposition, or by painting a coating using carbon black, nigrosin, black oxides of various metals (such as aluminum, zinc, or platinum), graphene, graphite, carbon nanotubes or flurenes, felt or various other materials. The structure may further integrate optical baffles and reflection traps that can limit stray rays reaching SP1 or SP2.

For passive, filter-less clogging avoidance, an inertial trap can be used by taking advantage of the conservation of linear or angular momentum. Vortex-like traps can be used to force larger particulate out for high-speed pumping rate, and meander-like traps (such as the physical element proximal to I in the schematic) can be used with a low-speed pumping rate. These structures can be added to serve as passive filters of large particulate matter in order to extend operations of the device between routine maintenance servicing.

Functional Description of Gas Identification

The analyte gas may be pumped into the spectrometer through I and may exit the device through O. Pumping can be performed with any type of fan or pump. The pump may be located on the output line to provide laminar flow and pumps the gas out from O.

The analyte gas contains trace gases to be identified by the spectrometer. While passing in the spectrometer, the analyte gas intercepts rays of light and absorbs specific wavelength, which depend upon the type and concentration of gases in the sample. Further, the analyte gas may contain a heterogeneous suspension of particulate matter which intercept, absorb and scatter light. The scattering depends upon the size of the particulate and the absorbance depends upon the albedo and geometry of the various individual particles in the heterogenous particulate suspension. By observing the spectrum of the transmitted light and the spectrum of the scattered light, information relevant to the gas type and concentration and shape, size and albedo of the particulate matter can be inferred.

Signal Processing

The raw information gathered by the proposed system is in the form of light intensity with respect to wavelength and time from the spectrometers SP1 and SP2. These signals, called spectra, depend on the properties of the analyte gas and particulate matters, the light source, the optical system and the spectrometer sensor properties. By using the known properties of the light source and the optical system, the signal is first processed. The optical properties of the specific spectrometer sensor used are also used to further refine the signal. For the case of FPI sensors, the information about the Fabry-Perot Interferometer transfer function is used to apply a signal deconvolution (or convolution of the reference solution) and enhance the sensor sensitivity when compared to the manufacturer-reported resolution.

For trace gas detection, the spectrum values from sensor SP2 is used to further enhance the spectrum data obtained by sensor SP1. Some of the spectrum of SP1 that may be attributed to absorption may in fact be the result of scattering, and the scattered light spectrum obtained by SP2 can be used to assist interpretation of the signal from SP1. Ad hoc knowledge about the probable analyte content using the data analytics methods described herein, together with the known typical spectral signatures for various gases at ambient environmental concentrations may used to assist with interpretation of the spectrometric data into probable gas mixtures and concentrations.

For particulate matter detection, the spectrum values from SP2 are used to identify characteristics of the particulate, such as type, size, shape and albedo. The particulate matter scattering spectrum can be used as a unique fingerprint for a particular type of particulate. The alignment of sensor SP2 in the optical system is standard for a light-scattering detector known as a nephelometer. However, nephelometers do not use broad spectrum analysis and rely on an inference of shape and albedo to analyze scattered light. By using a broadband spectrum for light source S1, more information can be gained on the size, shape and albedo of the particulate matter. Acquiring a library of spectral responses for various particulate type, size, shape and albedo can be used to identify the probable mixtures of gases and particulate matter at ambient environmental concentration in the sample.

Example of Signal Processing for Methane Monitoring

The analyte gas contains an inert gas, water vapor, carbon dioxide and methane as well as particulate matter. The spectra from SP1 and SP2 are collected, as well as the temperature and pressure of the chamber. The signals SP1 and SP2 are first deconvoluted from the known transfer function of the optical system and the light source at the known temperature and pressure of the chamber. The transmission spectrum from SP1 is compensated by the scattered spectrum of SP2. Similarly, the transmission spectrum from SP1 is used to compensate the scattered spectrum of SP2. The individual reference spectra at known concentration of water vapor, carbon dioxide and methane may be recovered from our own investigations or from a public database. The known transfer function of SP1 is applied as a convolution to the reference spectra of water vapor, carbon dioxide and methane. Our algorithm generates synthetic spectra of the water vapor, carbon dioxide and methane mixture from the convoluted reference spectra for various concentrations at the measured temperature and pressure. By minimizing the difference of the generated synthetic spectra and the actual refined spectrum from SP1, the actual concentrations of water, carbon dioxide and methane are found.

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Also, it is noted that the embodiments may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Unless defined otherwise, all technical and scientific terms used herein have the same meaning as commonly or conventionally understood. As used herein, the articles "a" and "an" refer to one or to more than one (i.e., to at least one) of the grammatical object of the article. By way of example, "an element" means one element or more than one element. "About" and/or "approximately" as used herein when referring to a measurable value such as an amount, a temporal duration, and the like, encompasses variations of ±20% or ±10%, ±5%, or +0.1% from the specified value, as such variations are appropriate to in the context of the systems, devices, circuits, methods, and other implementations described herein. "Substantially" as used herein when referring to a measurable value such as an amount, a temporal duration, a physical attribute (such as frequency), and the like, also encompasses variations of ±20% or ±10%, ±5%, or +0.1% from the specified value, as such variations are appropriate to in the context of the systems, devices, circuits, methods, and other implementations described herein.

As used herein, including in the claims, "and" as used in a list of items prefaced by "at least one of" or "one or more of" indicates that any combination of the listed items may be used. For example, a list of "at least one of A, B, and C" includes any of the combinations A or B or C or AB or AC or BC and/or ABC (i.e., A and B and C). Furthermore, to the extent more than one occurrence or use of the items A, B, or C is possible, multiple uses of A, B, and/or C may form part of the contemplated combinations. For example, a list of "at least one of A, B, and C" may also include AA, AAB, AAA, BB, etc.

While illustrative and presently preferred embodiments of the disclosed systems, methods, and/or machine-readable media have been described in detail herein, it is to be understood that the inventive concepts may be otherwise variously embodied and employed, and that the appended claims are intended to be construed to include such variations, except as limited by the prior art. While the principles of the disclosure have been described above in connection with specific apparatuses and methods, it is to be clearly understood that this description is made only by way of example and not as limitation on the scope of the disclosure.

What is claimed is:

1. An air quality monitoring method comprising:
accepting analyte gas into a cell;
emitting light rays into the analyte gas;
reflecting the light rays into the analyte gas repeatedly across the cell;
directing the light rays across a path within the cell into at least one sensor in response to repeated reflections;
generating a first spectra signal and a second spectra signal in response to directing the light rays into the at least one sensor; and
deconvoluting the first spectra signal and the second spectra signal based on properties of a light source emitting the light rays and optical properties of the at least one sensor at current temperature and pressure within the cell to generate a deconvoluted first spectra signal and a deconvoluted second spectra signal;
enhancing the deconvoluted first spectra signal based on the deconvoluted second spectra signal to compensate an amount of spectra-absorption for presence of particulate matter; and
determining a gaseous chemical based on the deconvoluted first spectra signal, post enhancing.

2. The air quality monitoring method of claim 1 and further comprising collimating the light rays prior to emitting into the analyte gas.

3. The air quality monitoring method of claim 2 and further comprising concentrating the light rays in response to the collimating, prior to emitting the light rays into the analyte gas.

4. The air quality monitoring method of claim 1 and further comprising:
pumping the analyte gas, via one of at least one pump, into the cell; and
pumping the analyte gas, via one of at least one pump, out of the cell,
wherein the at least one pump provide laminar flow to the analyte gas within the cell.

5. The air quality monitoring method of claim 1, wherein reflecting and directing the light rays along the path increases spectra-absorption and Signal to Noise (SNR) Ratio.

6. The air quality monitoring method of claim 1, wherein the cell comprises at least two reflective surfaces at opposite ends to enable reflecting the light rays repeatedly into the cell.

7. The air quality monitoring method of claim 1, wherein the at least one sensor is a spectrophotometric detector.

8. The air quality monitoring method of claim 1, wherein the at least one sensor is a nephelometer detector.

9. The air quality monitoring method of claim 1 further comprising:
receiving a reference spectra at predetermined concentration of each of water vapor, carbon dioxide and methane from a database;
applying transfer function of the first spectra signal as a convolution to the reference spectra of each of water vapor, carbon dioxide, and methane, to generate convoluted reference spectra;
generating synthetic spectra of each of water vapor, carbon dioxide and methane from the convoluted reference spectra for a plurality of concentrations at a measured temperature and a measured pressure; and
determining an actual concentration of each of water, carbon dioxide and methane, by minimizing difference of the generated synthetic spectra and an actual spectrum from the first spectra signal.

10. An air quality monitoring method comprising:
accepting analyte gas into a cell;
emitting light rays into the analyte gas;
reflecting the light rays into the analyte gas repeatedly across the cell;
directing the light rays across a path within the cell into at least one sensor in response to repeated reflections;
generating a first spectra signal and a second spectra signal in response to directing the light rays into the at least one sensor; and
deconvoluting the first spectra signal and the second spectra signal based on properties of a light source emitting the light rays and optical properties of the at least one sensor at current temperature and pressure within the cell to generate a deconvoluted first spectra signal and a deconvoluted second spectra signal;
enhancing the deconvoluted second spectra signal based on the deconvoluted first spectra signal to compensate presence of particulate matter with an amount of spectra-absorption; and
identifying the particulate matter based on the deconvoluted second spectra signal, post enhancing.

11. The air quality monitoring method of claim 10, wherein the at least one sensor is a nephelometer detector.

12. The air quality monitoring method of claim 10, wherein the at least one sensor is a spectrophotometric detector.

13. The air quality monitoring method of claim 10, wherein identifying the particulate matter comprises determining at least one of a shape, a size, and an albedo associated with the particulate matter.

14. A system for air quality monitoring, the system comprising:
a light source that emits light rays;
a cell that accepts analyte gas, the cell comprising:
two reflective surfaces located at opposite ends of the cell;
wherein the reflective surfaces are to repeatedly reflect the light rays along a path across the cell and to direct the light rays into at least one sensor in response to repeated reflections;
wherein a first spectra signal and a second spectra signal is generated in response to directing the light rays into the at least one sensor; and
a processing module to:
deconvolute the first spectra signal and the second spectra signal based on properties of the light source emitting the light rays and optical properties of the at least one sensor at current temperature and pressure within the cell to generate a deconvoluted first spectra signal and a deconvoluted second spectra signal;
enhance the deconvoluted first spectra signal based on the deconvoluted second spectra signal to compensate an amount of spectra-absorption for presence of particulate matter; and
determine a gaseous chemical based on the deconvoluted first spectra signal, post enhancing.

15. The system of claim 14, further comprising:
at least one pump for:
pumping the analyte gas into the cell; and
pumping the analyte gas out of the cell,
wherein the at least one pump provide laminar flow to the analyte gas within the cell.

16. The system of claim 14, wherein the at least one sensor is a spectrophotometric detector.

17. The system of claim 14, wherein the at least one sensor is a nephelometer detector.

18. A system for air quality monitoring, the system comprising:
- a light source that emits light rays;
- a cell that accepts analyte gas, the cell comprising:
  - two reflective surfaces located at opposite ends of the cell;
  - wherein the reflective surfaces are to repeatedly reflect the light rays along a path across the cell and to direct the light rays into at least one sensor in response to repeated reflections;
  - wherein a first spectra signal and a second spectra signal is generated in response to directing the light rays into the at least one sensor; and
- a processing module to:
  - deconvolute the first spectra signal and the second spectra signal based on properties of the light source emitting the light rays and optical properties of the at least one sensor at current temperature and pressure within the cell to generate a deconvoluted first spectra signal and a deconvoluted second spectra signal;
  - enhance the deconvoluted second spectra signal based on the deconvoluted first spectra signal to compensate presence of particulate matter with an amount of spectra-absorption; and
  - identify particulate matter based on the deconvoluted second spectra signal, post enhancing.

19. The system of claim 18, wherein identifying the particulate matter comprises:
- determining at least one of a shape, a size, and an albedo associated with the particulate matter.

20. The system of claim 19, wherein the processing module is to:
- acquire a library of spectral responses for a type, the size, the shape, and the albedo associated with the particulate matter; and
- identify a probable mixture of gases and particulate matter at ambient environmental concentration in a sample, using the library of spectral responses.

21. The system of claim 18, wherein the at least one sensor is one of:
- a nephelometer detector; and a spectrophotometric detector.

* * * * *